United States Patent
Burkett

(10) Patent No.: US 9,351,687 B2
(45) Date of Patent: May 31, 2016

(54) INTRAVASCULAR DEVICES, SYSTEMS, AND METHODS

(71) Applicant: Volcano Corporation, San Diego, CA (US)

(72) Inventor: David H. Burkett, Temecula, CA (US)

(73) Assignee: Volcano Corporation, Durham, NC (US)

( * ) Notice: Subject to any disclaimer, the term of this patent is extended or adjusted under 35 U.S.C. 154(b) by 280 days.

(21) Appl. No.: 13/931,052

(22) Filed: Jun. 28, 2013

(65) Prior Publication Data

US 2014/0005543 A1 Jan. 2, 2014

Related U.S. Application Data

(60) Provisional application No. 61/665,697, filed on Jun. 28, 2012.

(51) Int. Cl.
*A61B 5/02* (2006.01)
*A61B 5/00* (2006.01)
*A61B 8/12* (2006.01)
*A61B 5/0215* (2006.01)
*A61M 25/00* (2006.01)
*A61M 25/09* (2006.01)

(52) U.S. Cl.
CPC .............. *A61B 5/6851* (2013.01); *A61B 5/0215* (2013.01); *A61B 8/12* (2013.01); *A61M 2025/0002* (2013.01); *A61M 2025/09175* (2013.01); *Y10T 29/49826* (2015.01)

(58) Field of Classification Search
CPC ...... A61B 5/0215; A61B 5/6851; A61B 8/12; A61M 2025/0002; A61M 2025/09175; Y10T 29/49826
See application file for complete search history.

(56) References Cited

U.S. PATENT DOCUMENTS

| | | | | |
|---|---|---|---|---|
| 5,830,224 A * | 11/1998 | Cohn | ...................... | A61B 17/11 604/22 |
| 6,078,831 A | 6/2000 | Belef et al. | | |
| 8,403,856 B2 * | 3/2013 | Corl | ......................... | A61B 8/12 600/437 |
| 2004/0034303 A1 * | 2/2004 | Korotko | ................... | A61B 5/01 600/435 |
| 2004/0181177 A1 | 9/2004 | Lee et al. | | |
| 2004/0267115 A1 | 12/2004 | Carr | | |
| 2006/0106375 A1 * | 5/2006 | Werneth | ............. | A61B 18/1492 606/32 |

(Continued)

OTHER PUBLICATIONS

International Searching Authority/United States Patent Office, "Notification of Transmittal of the International Search Report and the Written Opinion of the International Searching Authority, or the Declaration," for PCT/US2013/048554, mailed Oct. 16, 2013, 11 pages.

*Primary Examiner* — Sanjay Cattungal
(74) *Attorney, Agent, or Firm* — Haynes and Boone, LLP

(57) ABSTRACT

Intravascular devices, systems, and methods are disclosed. In some embodiments, the intravascular devices include at least one electronic, optical, or electro-optical component positioned within a distal portion of the device and one or more connectors positioned at a distal portion of the device. In some instances, the connectors are flexible coils, such as a ribbon coil, formed of a conductive material. In some particular instances, the conductive coil is embedded within a polymer tubing. Further, in some embodiments the electronic, optical, or electro-optical component is positioned within a flexible element at the distal portion of the device. In some instances the flexible element is a coil. Methods of making and/or assembling such intravascular devices/systems are also provided.

20 Claims, 8 Drawing Sheets

(56) References Cited

U.S. PATENT DOCUMENTS

| | | | |
|---|---|---|---|
| 2007/0197891 A1* | 8/2007 | Shachar | A61B 5/0402 600/374 |
| 2007/0265516 A1* | 11/2007 | Wang | A61B 5/0402 600/374 |
| 2007/0287914 A1* | 12/2007 | Cohen | A61B 8/12 600/101 |
| 2008/0077050 A1 | 3/2008 | Von Malmborg et al. | |
| 2008/0097475 A1* | 4/2008 | Jaggi | A61B 5/07 606/130 |
| 2008/0319496 A1* | 12/2008 | Zhu | A61N 1/3962 607/5 |
| 2009/0005832 A1* | 1/2009 | Zhu | A61N 1/3627 607/27 |
| 2009/0005846 A1* | 1/2009 | Zhu | A61N 1/371 607/126 |
| 2009/0156981 A1* | 6/2009 | Fay | A61B 18/1492 604/20 |
| 2009/0275838 A1* | 11/2009 | Marshall | A61B 8/12 600/463 |
| 2010/0262040 A1 | 10/2010 | Von Malmborg | |
| 2013/0303920 A1* | 11/2013 | Corl | A61B 8/12 600/468 |
| 2014/0163664 A1* | 6/2014 | Goldsmith | A61B 17/00491 623/1.11 |

\* cited by examiner

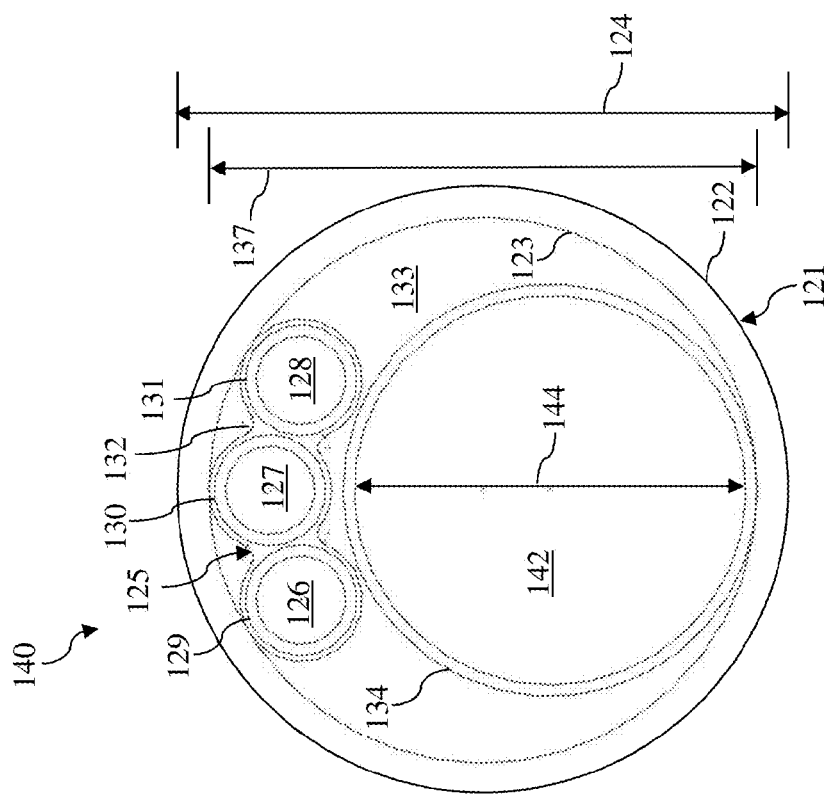
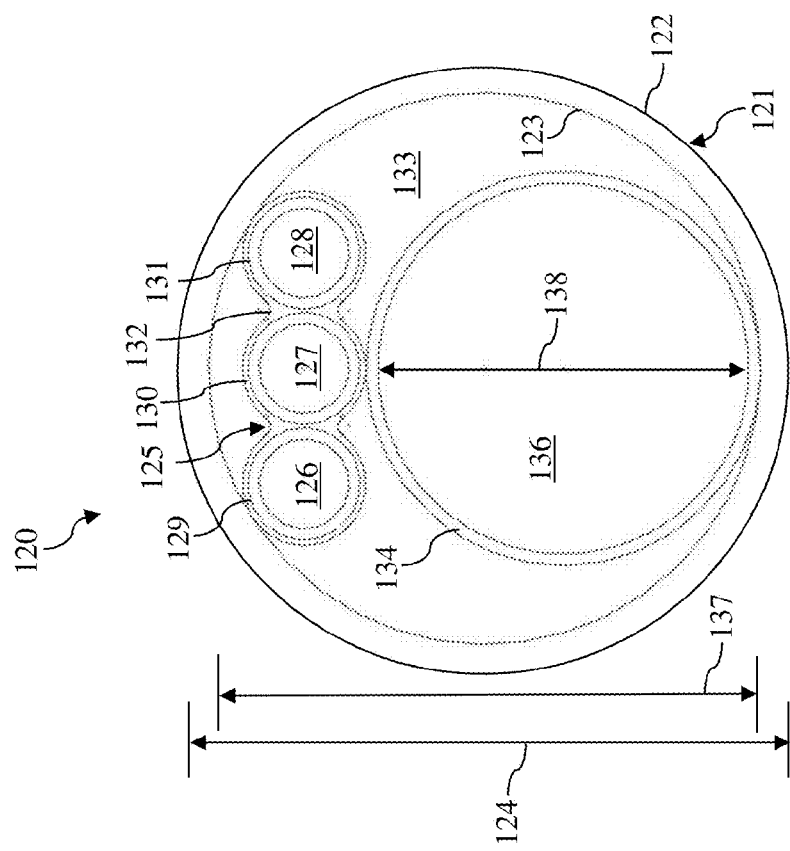

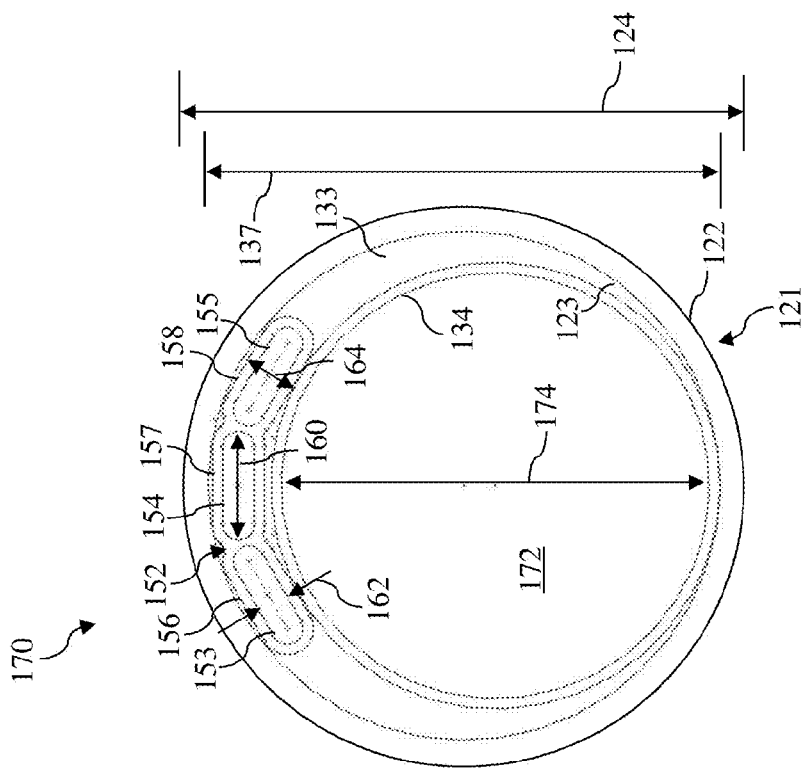
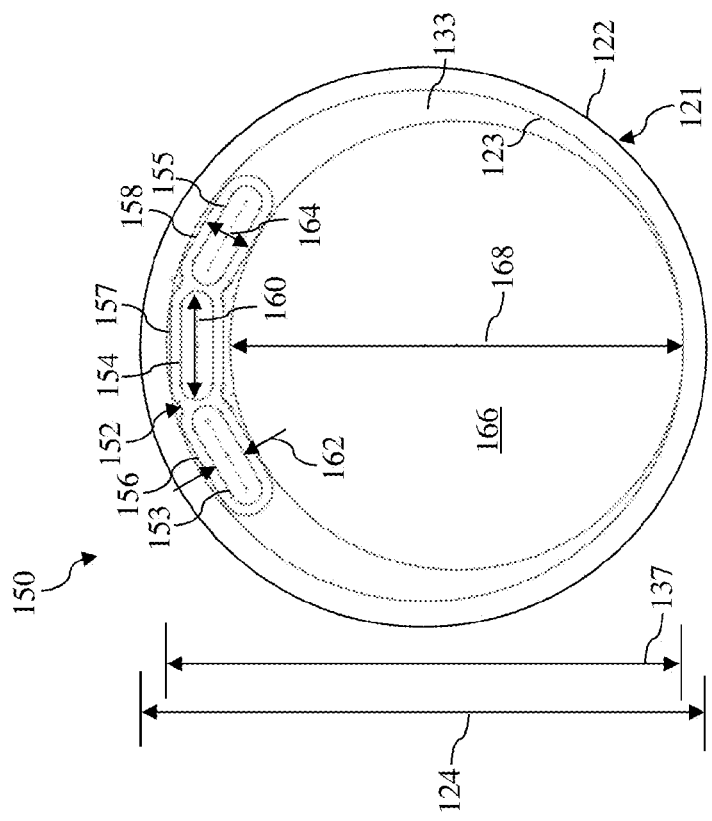

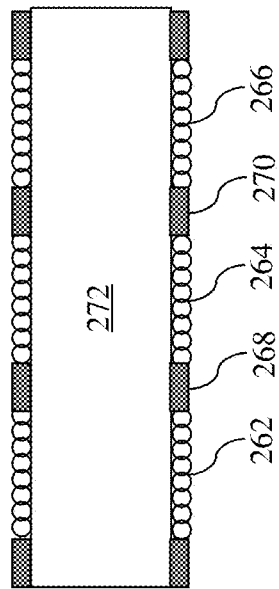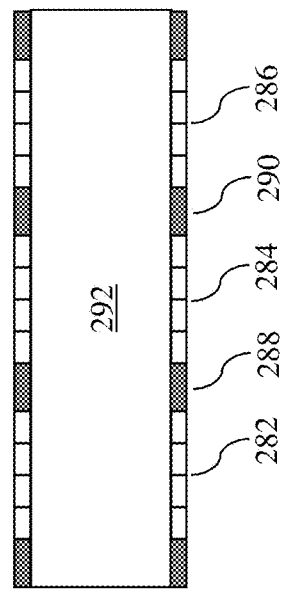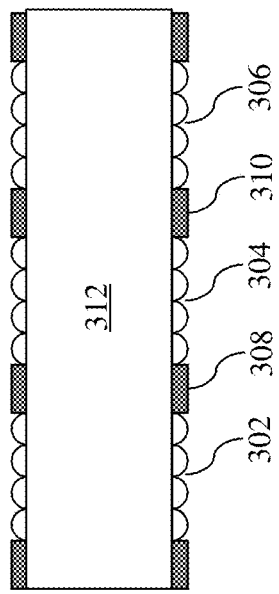

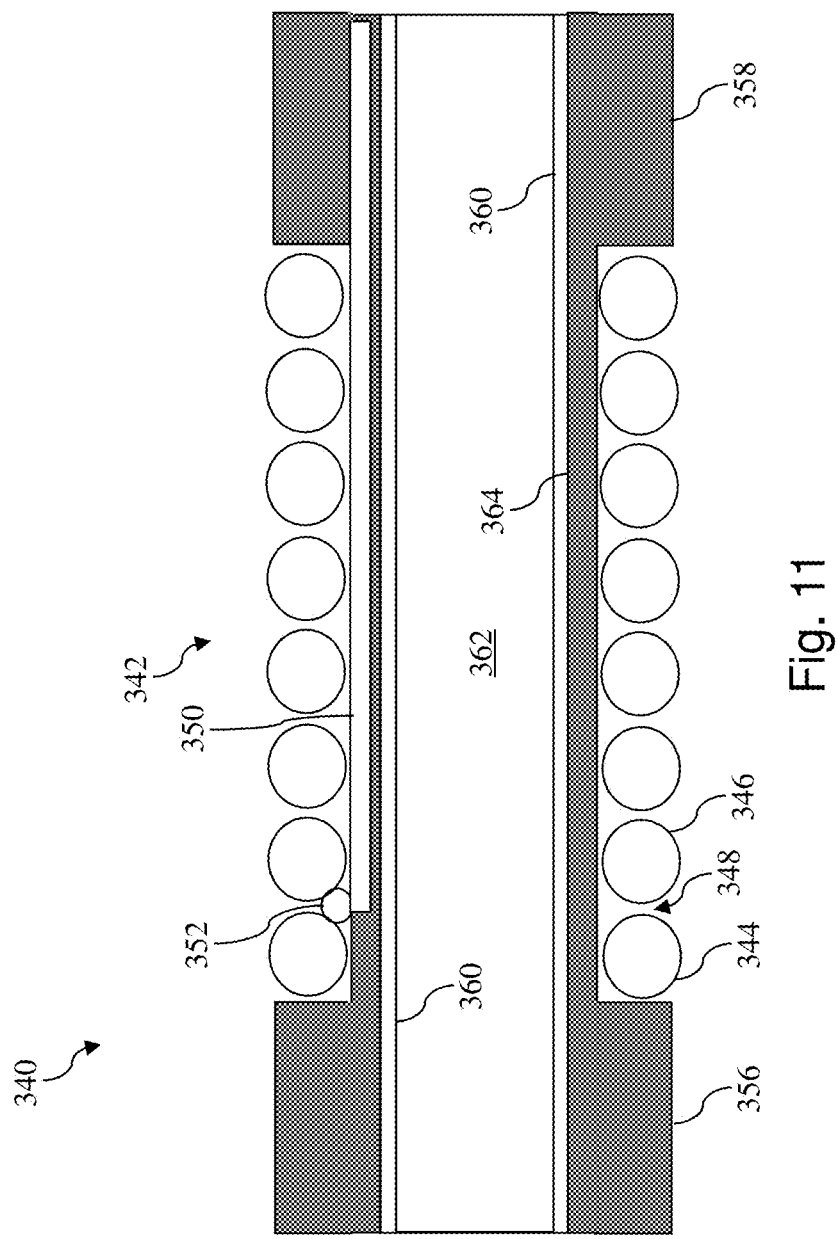

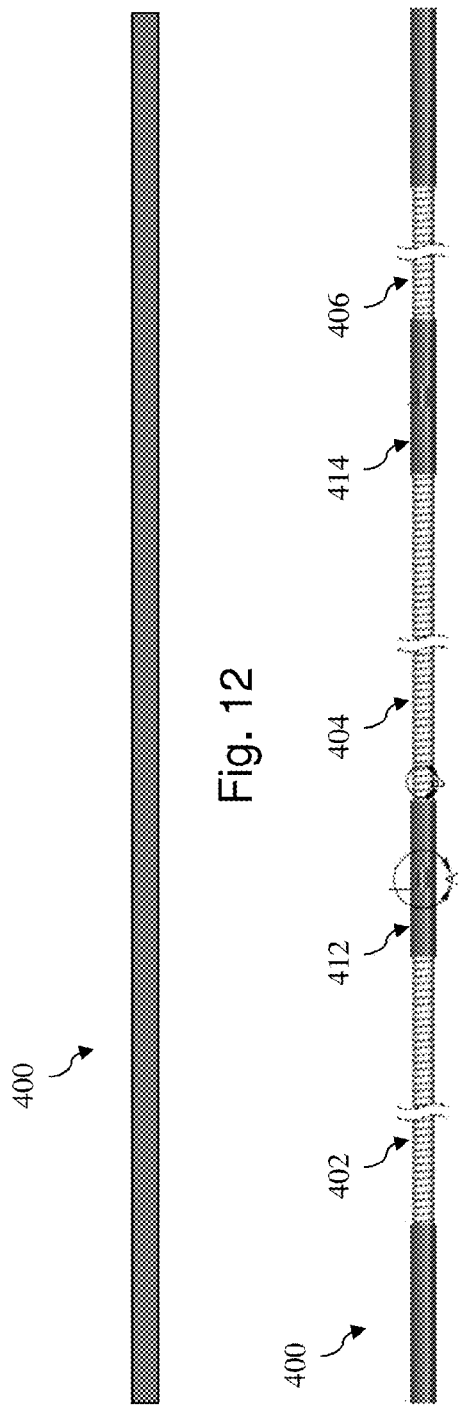
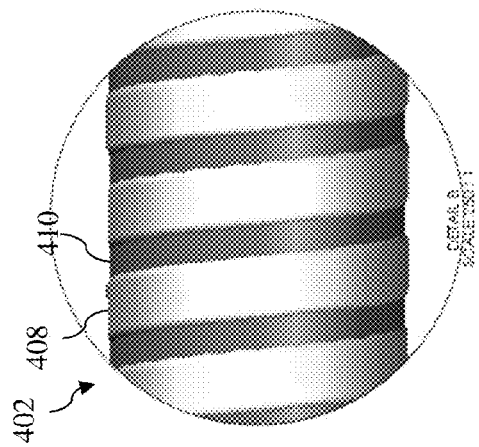

INTRAVASCULAR DEVICES, SYSTEMS, AND METHODS

CROSS REFERENCE TO RELATED APPLICATIONS

The present application claims priority to and the benefit of U.S. Provisional Patent Application No. 61/665,697, filed Jun. 28, 2012, which is hereby incorporated by reference herein in its entirety.

TECHNICAL FIELD

The present disclosure relates to intravascular devices, systems, and methods. In some embodiments, the intravascular devices are guidewires that include one or more electronic, optical, or electro-optical components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel, visualize the inner lumen of the blood vessel, and/or otherwise obtain data related to the blood vessel. To date, guidewires containing pressure sensors, imaging elements, and/or other electronic, optical, or electro-optical components have suffered from reduced performance characteristics compared to standard guidewires that do not contain such components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) is fragile and prone to kinking, which can destroy the functionality of the guidewire. For this reason, surgeons are reluctant to remove the proximal connector from the guidewire during a procedure for fear of breaking the guidewire when reattaching the proximal connector. Having the guidewire coupled to the proximal connector further limits the maneuverability and handling of the guidewire.

Accordingly, there remains a need for improved intravascular devices, systems, and methods that include one or more electronic, optical, or electro-optical components.

SUMMARY

Embodiments of the present disclosure are directed to intravascular devices, systems, and methods.

In one embodiment, a guidewire is provided. The guidewire comprises a first flexible element; a second flexible element coupled to the first flexible element in a position proximal to the first flexible element; a third flexible element coupled to the second flexible element in a position proximal to the second flexible element; a distal core extending within the first flexible element; a mounting structure positioned within the second flexible element and fixedly secured to the distal core, the mounting structure configured to have at least one component selected from the group of components consisting of an electronic component, an optical component, and an electro-optical component mounted thereto; at least one electronic, optical, or electro-optical component mounted to the mounting structure; a core fixedly attached to the mounting structure and extending proximally from the mounting structure through the second and third flexible elements; and at least one conductor having a proximal section and a distal section, wherein the distal section of the at least one conductor is coupled to the at least one electronic component and the proximal section of the at least one conductor is coupled to at least one connector; wherein the first, second, and third flexible elements have an outer diameter of 0.018" or less.

In some instances, the second flexible element comprises a ribbon coil. In that regard, the ribbon coil is embedded in a polymer tubing in some embodiments. The polymer tubing may have a thickness between about 0.0005" and about 0.003". In some embodiments, the core includes a first section that is fixedly attached to the mounting structure and a second section extending proximally from the first section, wherein the first section is formed of a first material and the second section is formed of a second material different than the first material. In some instances, the core further includes a third section extending proximally from the second section, wherein the third section is formed of a third material different than the second material. The third material is the same as the first material in some implementations. In some particular embodiments, the first material is a shape memory alloy, the second material is stainless steel, and the third material is a shape memory alloy.

In some embodiments, the at least one connector comprises a coil. In that regard, a wire forming the coil has a rectangular cross-sectional profile, a circular cross-sectional profile, a semi-circular cross-sectional profile with a rounded portion of the semi-circular cross-sectional profile extending outwardly, a semi-circular cross-sectional profile with a rounded portion of the semi-circular cross-sectional profile extending inwardly, and/or other suitable cross-sectional profile in some instances. In some embodiments, a section of the core positioned within the coil is formed of shape memory alloy, such as NiTiCo or Nitinol. In some instances, the proximal section of the at least one conductor is soldered to an inner portion of the coil. Sometimes, the coil is at least partially embedded within a polymer tubing. In some embodiments, an insulating layer is positioned between the coil and a proximal portion of the core.

In another embodiment, a method of assembling a guidewire is provided. The method includes providing a polymer tubing having a conductive coil embedded therein; removing a first portion of the polymer tubing to expose a first portion of the conductive coil; electrically coupling a proximal portion of a first conductor to the first portion of the conductive coil, wherein a distal portion of the first conductor is coupled to at least one component selected from the group of components consisting of an electronic component, an optical component, and an electro-optical component. In some instances, electrically coupling the proximal portion of the first conductor to the first portion of the conductive coil comprises soldering the first portion of the first conductor to the first portion of the conductive coil. In some embodiments, removing the first portion of the polymer tubing comprises laser ablating the polymer. In that regard, the polymer is ablated such that the first portion of the conductive coil extends between about 0.0001" and about 0.0005" above the polymer in some instances.

In some implementations, the method further includes removing a second portion of the polymer tubing to expose a second portion of the conductive coil; and electrically coupling a proximal portion of a second conductor to the second portion of the conductive coil, wherein a distal portion of the second conductor is coupled to at least one component selected from the group of components consisting of an electronic component, an optical component, and an electro-optical component. In that regard, the method may also include electrically isolating the first portion of the conductive coil from the second portion of the conductive coil. In some instances, electrically isolating the first portion of the conductive coil from the second portion of the conductive coil comprises forming an opening in a sidewall of the polymer tubing that severs a portion of the conductive coil positioned between the first and second portions of the conductive coil. The method may also include removing a third portion of the polymer tubing to expose a third portion of the conductive coil; electrically coupling a proximal portion of a third conductor to the third portion of the conductive coil, wherein a distal portion of the third conductor is coupled to at least one component selected from the group of components consisting of an electronic component, an optical component, and an electro-optical component; and electrically isolating each of the first, second, and third portions of the conductive coil from the other of the first, second, and third portions of the conductive coil. In that regard, electrically isolating each of the first, second, and third portions of the conductive coil from the other of the first, second, and third portions of the conductive coil comprises forming openings in a sidewall of the polymer tubing to sever portions of the conductive coil positioned between each of the first, second, and third portions of the conductive coil in some instances. Further, the method may also include coupling the polymer tubing to a proximal portion of an intravascular device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 2 is a diagrammatic cross-sectional longitudinal view of an intravascular device according to an embodiment of the present disclosure.

FIG. 3 is a diagrammatic cross-sectional longitudinal view of an intravascular device similar to that of FIG. 2, but illustrating another embodiment of the present disclosure.

FIG. 4 is a diagrammatic cross-sectional longitudinal view of an intravascular device similar to that of FIGS. 2 and 3, but illustrating another embodiment of the present disclosure.

FIG. 5 is a diagrammatic cross-sectional longitudinal view of an intravascular device similar to that of FIGS. 2-4, but illustrating another embodiment of the present disclosure.

FIG. 7 is a diagrammatic cross-sectional side view of a proximal connector portion of an intravascular device according to an embodiment of the present disclosure.

FIG. 8 is a diagrammatic cross-sectional side view of a proximal connector portion of an intravascular device similar to that of FIG. 7, but illustrating another embodiment of the present disclosure.

FIG. 9 is a diagrammatic cross-sectional side view of a proximal connector portion of an intravascular device similar to that of FIGS. 7 and 8, but illustrating another embodiment of the present disclosure.

FIG. 10 is a diagrammatic cross-sectional side view of a proximal connector portion of an intravascular device similar to that of FIGS. 7-9, but illustrating another embodiment of the present disclosure.

FIG. 11 is a diagrammatic cross-sectional close-up side view of a section of the proximal connector portion of an intravascular device of FIG. 7.

FIG. 12 is a diagrammatic side view of an element for forming a proximal connector portion of an intravascular device according to an embodiment of the present disclosure.

FIG. 13 is a diagrammatic side view of a proximal connector portion formed from the element of FIG. 12 according to an embodiment of the present disclosure.

FIG. 14 is a diagrammatic close-up side view of a conductor portion of the proximal connector portion of FIG. 13.

DETAILED DESCRIPTION

Figure 1:
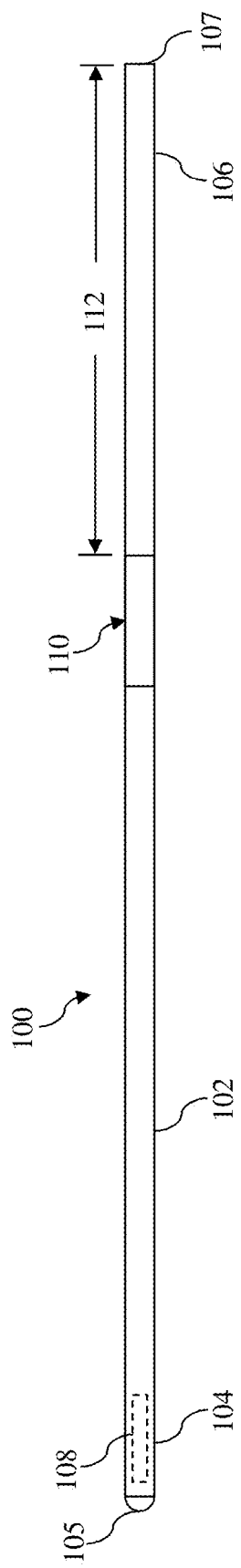
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guidewires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a minor, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. Some specific embodiments of electrical connectors in accordance with the present disclosure are discussed below in the context of FIGS. 5-11. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should again be noted that component 108 is comprised of a plurality of elements in some instances. In some instances, the connector 110 is configured to provide a physical connection to another device, either directly or indirectly. In other instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the flexible elongate member 102 between the connector 110 and the component 108. In some instances, between one and ten electrical conductors and/or optical pathways extend along the length of the flexible elongate member 102 between the connector 110 and the component 108. For the sake of clarity and simplicity, the embodiments of the present disclosure described below include three electrical conductors. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 108 and the corresponding elements that define component 108 to provide such functionality.

Referring now to FIGS. 2-5, shown therein are various cross-sectional profiles of intravascular devices of the present disclosure that illustrate techniques for extending communication pathways (e.g., electrical conductors and/or optical fibers) along the length of the device. In that regard, one of the major issues associated with existing functional guidewires is poor mechanical performance as compared to frontline guidewires. This performance loss is due in a large part to the typical design of the guidewires that severely limits the space available for the core or core wire due to the need to run the communication lines along the length of the device. As noted above, for the sake of clarity and simplicity, the embodiments of FIGS. 2-5 include three electrical conductors. More specifically, the embodiments of FIGS. 2-5 include three electrical conductors arranged as a trifilar. Existing trifilars are typically formed by three individual copper wires each wrapped with a color coded insulation material. A final overcoat is put over all three wires to connect them together as a single trifilar component.

Referring more specifically to FIG. 2, shown therein is a cross-sectional longitudinal view of an intravascular device 120 according to an embodiment of the present disclosure. The intravascular device 120 includes a main body 121 having an outer wall 122 defining an outer boundary of the intravascular device 120 and an inner wall 123 defining a lumen for receiving additional components of the intravascular device 120 that will be discussed in greater detail below. In the illustrated embodiment the main body 121 has a circular cross-sectional profile with an outer diameter 124. Diameter 124 is between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In some embodiments, the main body 121 has a constant profile along all or a majority of its length. For example, where the main body 121 has a circular cross-sectional profile, as shown in FIG. 2, the various portions of the main body maintain a constant outer diameter along all or a majority of the length of the intravascular device 120. In some embodiments, at the least the portions of the main body 121 that are intended to be disposed within the patient have a constant profile (or at least tapered/gradual transitions between portions with different outer profiles) to avoid potential injury to the patient while moving the intravascular device 120 through the patient. Further, it is recognized that the composition of the main body 121 changes along the length of the intravascular device in some instances. For example, in some embodiments the main body 121 transitions between one or more of a hypotube, a coil, a balloon, a polymer sleeve, and/or other structures and combinations thereof. The main body 121 maintains a constant profile across the transitions in some instances. In some instances, the main body 121 includes a polymer tubing with a conductive coil embedded therein as discussed with respect to FIGS. 12-16 below.

The intravascular device 120 also includes a trifilar 125 disposed within the lumen of the main body 121 defined by the inner wall 123. In that regard, the trifilar 125 consists of three electrical conductors or wires 126, 127, and 128, which may be formed of any suitable conductive material including without limitation copper, copper alloys, silver, silver alloys, aluminum, and/or combinations thereof. Each of the wires 126, 127, and 128 is wrapped with an insulating layer 129, 130, and 131, respectively. Any suitable insulating layer may be utilized, including without limitation polyimide, polyurethane, nylon, polyethylene, polypropylene, silicone rubber, fluoropolymers, and/or combinations thereof. In some embodiments, the insulating layers 129, 130, and 131 are color coded or otherwise include markings or identifiers to facilitate identification of the corresponding conductor 126, 127, and 128. An overcoat layer 132 is formed over the three conductors 126, 127, and 128 and insulating layers 129, 130, and 131 to connect the conductors together as a single trifilar component 125. Layer 132 is formed of an insulating material in some instances. For example, in some embodiments layer 132 is formed of one or more of polyurethane, polyethylene, polypropylene, silicone rubber, and/or combinations thereof. As shown, the trifilar 125 is positioned within the lumen 133 of the main body 121. In some instances, lumen 133 is open space. In other instances, the lumen 133 is partially or completely filled with a material. For example, in some instances a portion of the lumen 133 is filled with an adhesive, such as polyurethanes, cyanoacrylates, acrylates, silicone, and/or combinations thereof, that is utilized to secure components of the intravascular device 120 together. Accordingly, in some instances, the material filling lumen 133 also surrounds a layer 134 and core wire 136. In that regard, the layer 134 is formed of polyethylene terephthalate (PET) in some instances and may extend along all, a portion, or none of the length of the core wire 136 (i.e., layer 134 is omitted in some instances). In some embodiments, the layer 134 has a thickness between about 0.0001" (0.0025 mm) and about 0.0005" (0.0127 mm). In some embodiments, the layer 134 is intermittently used along the length of the core 136 as an insulator at certain joints and/or to hold the trifilar 125 to the core 136.

As shown, the inner wall 123 of the main body 121 defines a lumen having a diameter 137. The diameter 137 is dependent upon the outer diameter 124 of the main body 121 and the thickness of the main body between the outer wall 122 and the inner wall 123. As noted above, diameter 124 is between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). Further, the thickness of the main body 121 between the outer and inner surfaces 122 and 123 is between about 0.0005" or 0.012 7 mm and about 0.003" or 0.0762 mm. In some specific embodiments, the thickness is about 0.0254 mm, about 0.047 mm, or about 0.0508 mm. Based on the inner diameter 137, the size and orientation of the trifilar 125, and the thickness of layer 134, the core 136 has a maximum diameter 138.

In some instances, the arrangement of components shown in FIG. 2 limits the maximum outer diameter 138 of the core 136 to about 46% of the outer diameter 124 of the main body 121. For example, for a 0.014" outer diameter imaging device, the core diameter 138 is limited to about 0.0065". While this core diameter size is an improvement over previous devices that had a core diameter of about 0.0055" for a 0.014" outer diameter imaging device, which is equivalent to about 39% of the outer diameter, the present disclosure provides additional embodiments below that facilitate further increases in the diameter of the core wire. In that regard, it should be noted that the present inventors have found that increases in the core diameter as small as 0.0005" provide significant improvement to the handling performance characteristics to the imaging device 120. Some specific examples of arrangement that facilitate further increases in core diameter will now be described. For sake of clarity, these embodiments will be described in the context of an imaging device having a 0.014" outer diameter. However, it is understood that similar approaches may be utilized to increase the core diameters for imaging devices having smaller or larger outer diameters. In addition to and/or as an alternative to increasing the core diameters, the additional space provided by the embodiments of the present disclosure can be utilized to increase the number of components (e.g., including conductors and/or electronic components) positioned adjacent the distal portion of the device.

Referring now to FIG. 3, shown therein is a cross-sectional longitudinal view of an intravascular device 140 according to another embodiment of the present disclosure. The intravascular device 140 includes some features similar to those described above with respect to imaging device 120 and, therefore, the same reference numerals have been utilized to refer to similar components. The intravascular device 140 includes a main body 121 having an outer wall 122 defining an outer boundary of the intravascular device 120 and an inner wall 123 defining a lumen for receiving additional components of the intravascular device 140 that will be discussed in greater detail below. In the illustrated embodiment the main body 121 has a circular cross-sectional profile with an outer diameter 124. Diameter 124 is between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In some embodiments, the main body 121 has a constant profile along all or a majority of its length. For example, where the main body 121 has a circular cross-sectional profile, as shown in FIG. 3, the various portions of the main body maintain a constant outer diameter along all or a majority of the length of the intravascular device 140. In some embodiments, at the least the portions of the main body 121 that are intended to be disposed within the patient have a constant profile (or at least tapered/gradual transitions between portions with different outer profiles) to avoid potential injury to the patient while moving the intravascular device 140 through the patient. Further, it is recognized that the composition of the main body 121 changes along the length of the intravascular device in some instances. For example, in some embodiments the main body 121 transitions between one or more of a hypotube, a coil, a balloon, a polymer sleeve, and/or other structures and combinations thereof. The main body 121 maintains a constant profile across the transitions in some instances. In some instances, the main body 121 includes a polymer tubing with a conductive coil embedded therein as discussed with respect to FIGS. 12-16 below.

The intravascular device 140 also includes a trifilar 125 disposed within the lumen of the main body 121 defined by the inner wall 123. In that regard, the trifilar 125 consists of three electrical conductors or wires 126, 127, and 128, which may be formed of any suitable conductive material including without limitation copper, copper alloys, silver, silver alloys, aluminum, and/or combinations thereof. Each of the wires 126, 127, and 128 is wrapped with an insulating layer 129, 130, and 131, respectively. Any suitable insulating layer may be utilized, including without limitation polyimide, polyurethane, nylon, polyethylene, polypropylene, silicone rubber, fluoropolymers, and/or combinations thereof. In some embodiments, the insulating layers 129, 130, and 131 are color coded or otherwise include markings or identifiers to facilitate identification of the corresponding conductor 126, 127, and 128. An overcoat layer 132 is formed over the three conductors 126, 127, and 128 and insulating layers 129, 130, and 131 to connect the conductors together as a single trifilar component 125. Layer 132 is formed of an insulating material in some instances. For example, in some embodiments layer 132 is formed of one or more of polyurethane, polyethylene, polypropylene, silicone rubber, and/or combinations thereof. As shown, unlike the embodiment of FIG. 2 where the conductors 126, 127, and 128 were aligned such that a central longitudinal axis of each of the conductors 126, 127, and 128 would be in a common plane, in the embodiment of FIG. 3 the conductors 126, 127, and 128 are arranged in an arcuate, curved, and/or offset orientation such that the trifilar generally follows the curvature of the inner wall 123. In the illustrated embodiment of FIG. 3, central longitudinal axes of conductors 126 and 128 are positioned in a common plane, but the central longitudinal axis of conductor 127 is offset (upwards as viewed in FIG. 3) towards the outer boundary of the main body 121.

As shown, the trifilar 125 is positioned within the lumen 133 of the main body 121. In some instances, lumen 133 is open space. In other instances, the lumen 133 is partially or completely filled with a material. For example, in some instances a portion of the lumen 133 is filled with an adhesive, such as polyurethanes, cyanoacrylates, acrylates, silicone, and/or combinations thereof, that is utilized to secure components of the intravascular device 120 together. Accordingly, in some instances, the material filling lumen 133 also surrounds a layer 134 and core wire 136. In that regard, the layer 134 is formed of polyethylene terephthalate (PET) in some instances and may extend along all, a portion, or none of the length of the core wire 136 (i.e., layer 134 is omitted in some instances). In some embodiments, the layer 134 has a thickness between about 0.0001" (0.0025 mm) and about 0.0005" (0.0127 mm). In some embodiments, the layer 134 is intermittently used along the length of the core 136 as an insulator at certain joints and/or to hold the trifilar 125 to the core 136.

As shown, the inner wall 123 of the main body 121 defines a lumen having a diameter 137. The diameter 137 is dependent upon the outer diameter 124 of the main body 121 and the thickness of the main body between the outer wall 122 and the inner wall 123. As noted above, diameter 124 is between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). Further, the thickness of the main body 121 between the outer and inner surfaces 122 and 123 is between about 0.0005" or 0.012 7 mm and about 0.003" or 0.0762 mm. In some specific embodiments, the thickness is about 0.0254 mm, about 0.047 mm, or about 0.0508 mm. Based on the inner diameter 137, the size and orientation of the trifilar 125, and the thickness of layer 134, the core 142 has a maximum diameter 144.

This arrangement of components shown in FIG. 3 increases the maximum outer diameter 144 of the core 142 relative to the maximum outer diameter 138 of the core 136 of imaging device 120 of FIG. 2 from about 46% to about 50% of the outer diameter 124 of the main body 121. For example, for a 0.014" outer diameter imaging device, the core diameter 144 is increased to about 0.0070".

Referring now to FIG. 4, shown therein is a cross-sectional longitudinal view of an intravascular device 150 according to another embodiment of the present disclosure. The intravascular device 150 includes some features similar to those described above with respect to imaging devices 120 and 140 and, therefore, the same reference numerals have been utilized to refer to similar components. The intravascular device 150 includes a main body 121 having an outer wall 122 defining an outer boundary of the intravascular device 120 and an inner wall 123 defining a lumen for receiving additional components of the intravascular device 150 that will be discussed in greater detail below. In the illustrated embodiment the main body 121 has a circular cross-sectional profile with an outer diameter 124. Diameter 124 is between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In some embodiments, the main body 121 has a constant profile along all or a majority of its length. For example, where the main body 121 has a circular cross-sectional profile, as shown in FIG. 4, the various portions of the main body maintain a constant outer diameter along all or a majority of the length of the intravascular device 150. In some embodiments, at the least the portions of the main body 121 that are intended to be disposed within the patient have a constant profile (or at least tapered/gradual transitions between portions with different outer profiles) to avoid potential injury to the patient while moving the intravascular device 150 through the patient. Further, it is recognized that the composition of the main body 121 changes along the length of the intravascular device in some instances. For example, in some embodiments the main body 121 transitions between one or more of a hypotube, a coil, a balloon, a polymer sleeve, and/or other structures and combinations thereof. The main body 121 maintains a constant profile across the transitions in some instances. In some instances, the main body 121 includes a polymer tubing with a conductive coil embedded therein as discussed with respect to FIGS. 12-16 below.

The intravascular device 150 also includes a trifilar 152 disposed within the lumen of the main body 121 defined by the inner wall 123. In that regard, the trifilar 152 consists of three electrical conductors or wires 153, 154, and 155, which may be formed of any suitable conductive material including without limitation copper, copper alloys, silver, silver alloys, aluminum, and/or combinations thereof. Each of the conductors 153, 154, and 155 is wrapped with an insulating layer 156, 157, and 158, respectively. Any suitable insulating layer may be utilized, including without limitation polyimide, polyurethane, nylon, polyethylene, polypropylene, silicone rubber, fluoropolymers, and/or combinations thereof. In some embodiments, the insulating layers 156, 157, and 158 are color coded or otherwise include markings or identifiers to facilitate identification of the corresponding conductor 153, 154, and 155. In some embodiments, the insulating layers 156, 157, and 158 form a continuous integrated insulating structure that couples the conductors 153, 154, and 155 together. In other instances, the insulating layers 156, 157, and 158 are separately formed over the respective conductors 153, 154, and 155 and an overcoat layer is formed over the three conductors 153, 154, and 155 and insulating layers 156, 157, and 158 to connect the conductors together as a single trifilar component 152.

As shown, similar to the conductors 126, 127, and 128 of FIG. 3, the conductors 153, 154, and 155 are arranged in an arcuate, curved, and/or offset orientation such that the trifilar generally follows the curvature of the inner wall 123. In the illustrated embodiment of FIG. 4, central longitudinal axes of conductors 153 and 155 are positioned in a common plane, but the central longitudinal axis of conductor 154 is offset (upwards as viewed in FIG. 4) towards the outer boundary of the main body 121. However, unlike the conductors 126, 127, and 128 of FIG. 3 that have a circular cross-sectional profile, the conductors 153, 154, and 155 of FIG. 4 have a flattened configuration. In particular, each of the conductors 153, 154, and 155 has a generally rectangular cross sectional profile within rounded edges. In some instances, each of the conductors has a cross-sectional width 160 between about 0.0178 mm and about 0.0762 mm. Further, in some instances, each of the conductors has a cross-sectional thickness 162 between about 0.00508 mm and about 0.0254 mm. Further still, in some instances each of the insulating layers 156, 157, and 158 has a thickness between about 0.00508 mm and about 0.0127 mm such that the total thickness 164 of the trifilar 152 is between about 0.01016 mm and about 0.0381 mm. In some instances, the flattened trifilar is formed by using a specific gauge wire (e.g., 48 gauge or 0.0012" copper wire) with specific build thickness of insulation (e.g., triple build) that results in overall thickness of trifilar of between about 0.0018" and about 0.002". The trifilar structure is then roller flattened to a specific desired thickness, such as the ranges discussed above, which results in the thicknesses of both the insulation and the copper wire being reduced.

As shown, the trifilar 152 is positioned within the lumen 133 of the main body 121. In some instances, lumen 133 is open space. In other instances, the lumen 133 is partially or completely filled with a material. For example, in some instances a portion of the lumen 133 is filled with an adhesive, such as polyurethanes, cyanoacrylates, acrylates, silicone, and/or combinations thereof, that is utilized to secure components of the intravascular device 150 together. Accordingly, in some instances, the material filling lumen 133 also surrounds core wire 166. In that regard, FIG. 4 shows a cross-section where the layer 134 discussed with respect to FIGS. 2 and 3 has been omitted. Based on the inner diameter 137, the size and orientation of the trifilar 152, and the omission of the layer surrounding the core 166, the core 166 has a maximum diameter 168. This arrangement of components shown in FIG. 4 increases the maximum outer diameter 168 of the core 166 relative to the maximum outer diameter 138 of the core 136 of imaging device 120 of FIG. 2 from about 46% to about 61% of the outer diameter 124 of the main body 121. For example, for a 0.014" outer diameter imaging device, the core diameter 168 is increased to about 0.0085".

Referring now to FIG. 5, shown therein is a cross-sectional longitudinal view of an intravascular device 170 according to another embodiment of the present disclosure. The intravascular device 170 includes some features similar to those described above with respect to imaging devices 120, 140, and 150 and, therefore, the same reference numerals have been utilized to refer to similar components. The intravascular device 170 includes a main body 121 having an outer wall 122 defining an outer boundary of the intravascular device 120 and an inner wall 123 defining a lumen for receiving additional components of the intravascular device 170 that will be discussed in greater detail below. In the illustrated embodiment the main body 121 has a circular cross-sectional profile with an outer diameter 124. Diameter 124 is between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In some embodiments, the main body 121 has a constant profile along all or a majority of its length. For example, where the main body 121 has a circular cross-sectional profile, as shown in FIG. 5, the various portions of the main body maintain a constant outer diameter along all or a majority of the length of the intravascular device 170. In some embodiments, at the least the portions of the main body 121 that are intended to be disposed within the patient have a constant profile (or at least tapered/gradual transitions between portions with different outer profiles) to avoid potential injury to the patient while moving the intravascular device 170 through the patient. Further, it is recognized that the composition of the main body 121 changes along the length of the intravascular device in some instances. For example, in some embodiments the main body 121 transitions between one or more of a hypotube, a coil, a balloon, a polymer sleeve, and/or other structures and combinations thereof. The main body 121 maintains a constant profile across the transitions in some instances. In some instances, the main body 121 includes a polymer tubing with a conductive coil embedded therein as discussed with respect to FIGS. 12-16 below.

The intravascular device 170 also includes a trifilar 152 disposed within the lumen of the main body 121 defined by the inner wall 123. In that regard, the trifilar 152 consists of three electrical conductors or wires 153, 154, and 155, which may be formed of any suitable conductive material including without limitation copper, copper alloys, silver, silver alloys, aluminum, and/or combinations thereof. Each of the conductors 153, 154, and 155 is wrapped with an insulating layer 156, 157, and 158, respectively. Any suitable insulating layer may be utilized, including without limitation polyimide, polyurethane, nylon, polyethylene, polypropylene, silicone rubber, fluoropolymers, and/or combinations thereof. In some embodiments, the insulating layers 156, 157, and 158 are color coded or otherwise include markings or identifiers to facilitate identification of the corresponding conductor 153, 154, and 155. In some embodiments, the insulating layers 156, 157, and 158 form a continuous integrated insulating structure that couples the conductors 153, 154, and 155 together. In other instances, the insulating layers 156, 157, and 158 are separately formed over the respective conductors 153, 154, and 155 and an overcoat layer is formed over the three conductors 153, 154, and 155 and insulating layers 156, 157, and 158 to connect the conductors together as a single trifilar component 152.

As shown, the conductors 153, 154, and 155 are arranged in an arcuate, curved, and/or offset orientation such that the trifilar 152 generally follows the curvature of the inner wall 123. In the illustrated embodiment of FIG. 5, central longitudinal axes of conductors 153 and 155 are positioned in a common plane, but the central longitudinal axis of conductor 154 is offset (upwards as viewed in FIG. 4) towards the outer boundary of the main body 121. Each of the conductors 153, 154, and 155 has a generally rectangular cross sectional profile within rounded edges. In some instances, each of the conductors has a cross-sectional width 160 between about 0.0178 mm and about 0.0762 mm. Further, in some instances, each of the conductors has a cross-sectional thickness 162 between about 0.00508 mm and about 0.0254 mm. Further still, in some instances each of the insulating layers 156, 157, and 158 has a thickness between about 0.00508 mm and about 0.0127 mm such that the total thickness 164 of the trifilar 152 is between about 0.01016 mm and about 0.0381 mm. In some instances, the flattened trifilar is formed by using a specific gauge wire (e.g., 48 gauge or 0.0012" copper wire) with specific build thickness of insulation (e.g., triple build) that results in overall thickness of trifilar of between about 0.0018" and about 0.002". The trifilar structure is then roller flattened to a specific desired thickness, such as the ranges discussed above, which results in the thicknesses of both the insulation and the copper wire being reduced.

As shown, the trifilar 152 is positioned within the lumen 133 of the main body 121. In some instances, lumen 133 is open space. In other instances, the lumen 133 is partially or completely filled with a material. For example, in some instances a portion of the lumen 133 is filled with an adhesive, such as polyurethanes, cyanoacrylates, acrylates, silicone, and/or combinations thereof, that is utilized to secure components of the intravascular device 170 together. Accordingly, in some instances, the material filling lumen 133 also surrounds a layer 134 and core wire 172. In that regard, the layer 134 is formed of polyethylene terephthalate (PET) in some instances and may extend along all, a portion, or none of the length of the core wire 136 (i.e., layer 134 is omitted in some instances). In some embodiments, the layer 134 has a thickness between about 0.0001" (0.0025 mm) and about 0.0005" (0.0127 mm). In some embodiments, the layer 134 is intermittently used along the length of the core 172 as an insulator at certain joints and/or to hold the trifilar 152 to the core 172. Based on the inner diameter 137, the size and orientation of the trifilar 152, and the layer 134 surrounding the core 172, the core 172 has a maximum diameter 174. This arrangement of components shown in FIG. 5 increases the maximum outer diameter 174 of the core 172 relative to the maximum outer diameter 138 of the core 136 of imaging device 120 of FIG. 2 from about 46% to about 57% of the outer diameter 124 of the main body 121. For example, for a 0.014" outer diameter imaging device, the core diameter 168 is increased to about 0.0080".

Figure 6:
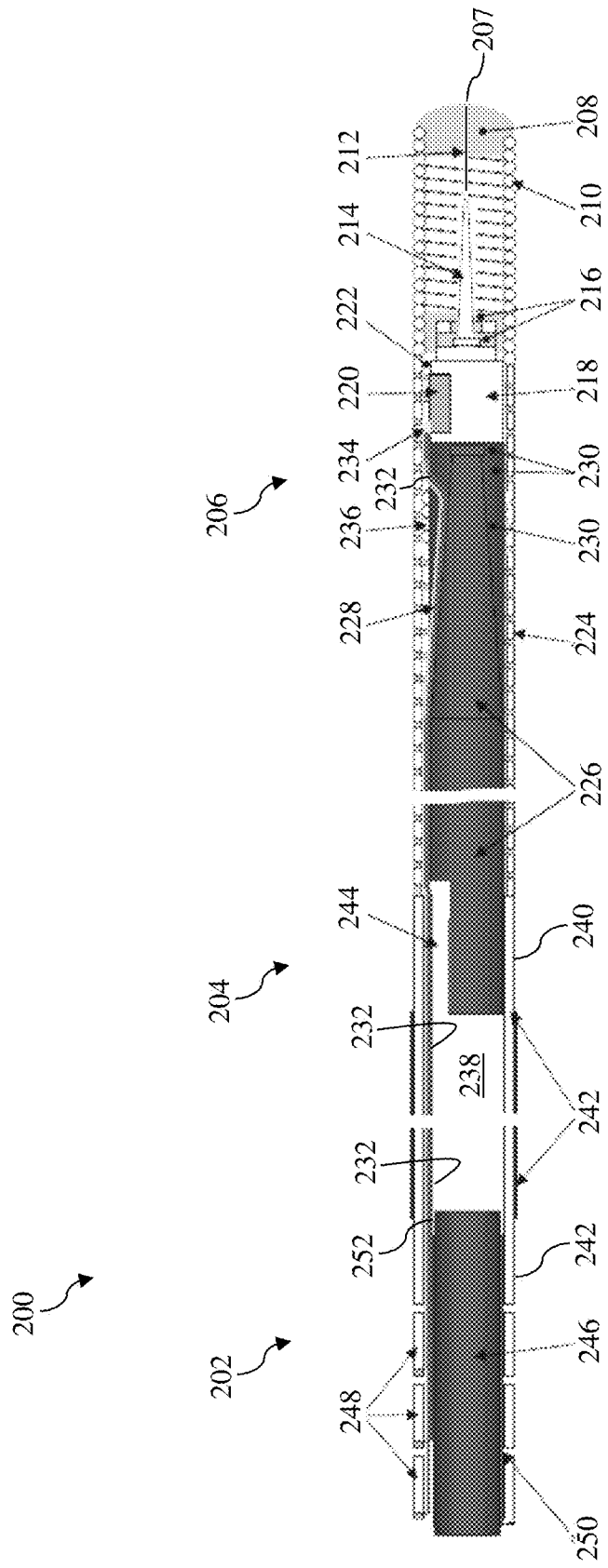
FIG. 6 is diagrammatic cross-sectional side view of an intravascular device according to an embodiment of the present disclosure.

Referring now to FIG. 6, shown therein is a cross-sectional side view of an intravascular device 200 according to an embodiment of the present disclosure. As shown, the intravascular device 200 includes a proximal portion 202, a middle portion 204, and a distal portion 206. Generally, the proximal portion 202 is configured to be positioned outside of a patient, while the distal portion 206 and a majority of the middle portion 204 are configured to be inserted into the patient, including within human vasculature. In that regard, the middle and distal portion 204 have an outer diameter between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In the illustrated embodiment of FIG. 6, the intravascular device 200 has an outer diameter of 0.014" (0.3556 mm).

As shown, the distal portion 206 of the intravascular device 200 has a distal tip 207 defined by an element 208. In the illustrated embodiment, the distal tip 207 has a rounded profile. In some instances, the element 208 is radiopaque such that the distal tip 207 is identifiable under x-ray, fluoroscopy, and/or other imaging modalities when positioned within a patient. In some particular instances, the element 208 is solder secured to a flexible element 210 and/or a flattened tip core 212. In that regard, in some instances the flexible element 210 is a coil spring. The flattened tip core 212 extends distally from a distal core 214. As shown, the distal core 214 tapers to a narrow profile as it extends distally towards the distal tip 207. In some instances, the distal core 214 is formed of a stainless steel that has been ground down have the desired tapered profile. In some particular instances, the distal core 214 is formed of high tensile strength 304V stainless steel. In an alternative embodiment, the distal core 214 is formed by wrapping a stainless steel shaping ribbon around a nitinol core. Solder points 216 secure the distal core 214 to a mounting structure 218. The mounting structure 218 is configured to receive and securely hold a component 220. In that regard, the component 220 is one or more of an electronic component, an optical component, and/or electro-optical component. For example, without limitation, the component 220 may be one or more of the following types of components: a pressure sensor, a temperature sensor, an imaging element, an optical fiber, an ultrasound transducer, a reflector, a minor, a prism, an ablation element, an RF electrode, a conductor, and/or combinations thereof.

The mounting structure 218 is fixedly secured within the distal portion 206 of the intravascular device 200 by an adhesive or solder 222. In that regard, the mounting structure 218 is disposed within the flexible element 210 and/or a flexible element 224. In some instances, the flexible element 224 is ribbon coil covered with a polymer coating. For example, in one embodiment the flexible element 224 is a stainless steel ribbon wire coil coated with polyethylene terephthalate (PET). In another embodiment, the flexible element is a polyimide tubing that has a ribbon wire coil embedded therein. For example, in some instances a polyimide or Pebax tubing with embedded coil similar to that discussed below with respect to FIGS. 12-16 is utilized for flexible element 224. In some particular embodiments, the ribbon wire coil is embedded to an inner diameter of the polyimide tubing. The adhesive 222 is utilized to secure the mounting structure 218 to the flexible element 210 and/or the flexible element 224. Accordingly, in some instances the adhesive is urethane acrylate, cyanoacrylate, silicone, epoxy, and/or combinations thereof. The mounting structure 218 is also secured to a core 226 that extends proximally from the mounting structure towards the middle portion 204 of the intravascular device 200. In that regard, a distal portion 228 of the core 226 tapers as it extends distally towards mounting structure 218. A distal end of the distal portion 228 of the core 226 is fixedly secured to the mounting structure 218. In some instances, the distal end of the core 226 is soldered to the mounting structure. As shown, adhesive 230 surrounds at least a portion of the distal portion 228 of the core 226. In some instances, the adhesive 230 is the adhesive 222 used to secure the mounting structure 218 to the flexible element 210 and/or flexible element 224. In other instances, adhesive 230 is a different type of adhesive than adhesive 222. In one particular embodiment, adhesive or solder 222 is particularly suited to secure the mounting structure to flexible element 210, while adhesive 230 is particularly suited to secure the mounting structure to flexible element 224.

A communication cable 232 extends along the length of the intravascular device 200 from the proximal portion 202 to the distal portion 206. In that regard, the distal end of the communication cable 232 is coupled to the component 220 at junction 234. The type of communication cable utilized is dependent on the type of electronic, optical, and/or electro-optical components that make up the component 220. In that regard, the communication cable 232 may include one or more of an electrical conductor, an optical fiber, and/or combinations thereof. Appropriate connections are utilized at the junction 234 based on the type of communication lines included within communication cable 232. For example, electrical connections are soldered in some instances, while optical connections pass through an optical connector in some instances. In some embodiments, the communication cable 232 is a trifilar structure as described above with respect to FIGS. 2-5. Further, it is understood that all and/or portions of each of the proximal, middle, and/or distal portions 202, 204, 206 of the intravascular device 200 may have cross-sectional profiles as shown in FIGS. 2-5. In one particular embodiment, the component 220 is a pressure sensor and at least the middle portion 204 of the intravascular device 200 has the cross-sectional profile of either FIG. 4 or FIG. 5.

Further, in some embodiments, the proximal portion 202 and/or the distal portion 206 incorporate spiral ribbon tubing as discussed with respect to FIGS. 12-16 below. In some instances, the use of such spiral ribbon tubing allows a further increase in the available lumen space within the device. For example, in some instances use of a spiral ribbon tubing having a wall thickness between about 0.001" and about 0.002" facilitates the use of a core wire having an outer diameter of at least 0.0095" within a 0.014" outer diameter guidewire using a trifilar with circular cross-sectional conductor profiles (see, e.g., FIGS. 2 and 3). The size of the core wire can be further increased to at least 0.010" by using a trifilar with the flattened oblong cross-section conductor profiles (see, e.g., FIGS. 4 and 5). The availability to use a core wire having an increased diameter allows the use of materials having a lower modulus of elasticity than a standard stainless steel core wire (e.g., superelastic materials such as Nitinol or NiTiCo are utilized in some instances) without adversely affecting the handling performance or structural integrity of the guidewire and, in many instances, provides improvement to the handling performance of the guidewire, especially when a superelastic material with an increased core diameter (e.g., a core diameter of 0.0075" or greater) is utilized within the distal portion 206.

The distal portion 206 of the intravascular device 200 also optionally includes at least one imaging marker 236. In that regard, the imaging marker 236 is configured to be identifiable using an external imaging modality, such as x-ray, fluoroscopy, angiograph, CT scan, MRI, or otherwise, when the distal portion 206 of the intravascular device 200 is positioned within a patient. In the illustrated embodiment, the imaging marker 236 is a radiopaque coil positioned around the tapered distal portion 228 of the core 226. Visualization of the imaging marker 236 during a procedure can give the medical personnel an indication of the size of a lesion or region of interest within the patient. To that end, the imaging marker 236 can have a known length (e.g., 0.5 cm or 1.0 cm) and/or be spaced from the element 208 by a known distance (e.g., 3.0 cm) such that visualization of the imaging marker 236 and/or the element 208 along with the anatomical structure allows a user to estimate the size or length of a region of interest of the anatomical structure. It is understood that a plurality of imaging markers 236 are utilized in some instances. In that regard, in some instances the imaging markers 236 are spaced a known distance from one another to further facilitate measuring the size or length of the region of interest.

In some instances, a proximal portion of the core 226 is secured to a core 238 that extends through the middle portion 204 of the intravascular device. In that regard, the transition between the core 226 and the core 238 may occur within the distal portion 206, within the middle portion 204, and/or at the transition between the distal portion 206 and the middle portion 204. For example, in the illustrated embodiment the transition between core 226 and core 238 occurs in the vicinity of a transition between the flexible element 224 and a flexible element 240. The flexible element 240 in the illustrated embodiment is a hypotube. In some particular instances, the flexible element is a stainless steel hypotube. Further, in the illustrated embodiment a portion of the flexible element 240 is covered with a coating 242. In that regard, the coating 242 is a hydrophobic coating in some instances. In some embodiments, the coating 242 is a polytetrafluoroethylene (PTFE) coating.

The proximal portion of core 226 is fixedly secured to the distal portion of core 238. In that regard, any suitable technique for securing the cores 226, 238 to one another may be used. In some embodiments, at least one of the cores 226, 238 includes a plunge grind or other structural modification that is utilized to couple the cores together. In some instances, the cores 226, 238 are soldered together. In some instances, an adhesive is utilized to secure the cores 226, 238 together. In some embodiments, combinations of structural interfaces, soldering, and/or adhesives are utilized to secure the cores 226, 238 together. In other instances, the core 226 is not fixedly secured to core 238. For example, in some instances, the core 226 and the core 246 are fixedly secured to the hypotube 240 and the core 238 is positioned between the cores 226 and 246, which maintains the position of the core 238 between cores 226 and 246.

In some embodiments, the core 238 is formed of a different material than the core 226. For example, in some instances the core 226 is formed of nitinol and the core 238 is formed of stainless steel. In other instances, the core 238 and the core 226 are formed of the same material. In some instances the core 238 has a different profile than the core 226, such as a larger or smaller diameter and/or a non-circular cross-sectional profile. For example, in some instances the core 238 has a D-shaped cross-sectional profile. In that regard, a D-shaped cross-sectional profile has some advantages in the context of an intravascular device 200 that includes one or more electronic, optical, or electro-optical component in that it provides a natural space to run any necessary communication cables while providing increased strength than a full diameter core.

In some instances, a proximal portion of the core 238 is secured to a core 246 that extends through at least a portion of the proximal portion 202 of the intravascular device 200. In that regard, the transition between the core 238 and the core 246 may occur within the proximal portion 202, within the middle portion 204, and/or at the transition between the proximal portion 202 and the middle portion 204. For example, in the illustrated embodiment the transition between core 238 and core 246 is positioned distal of a plurality of conducting bands 248. In that regard, in some instances the conductive bands 248 are portions of a hypotube. In other instances, the conductive bands are coils, such as those discussed in the context of FIGS. 7-16 below. Proximal portions of the communication cable 232 are coupled to the conductive bands 248. In that regard, in some instances each of the conductive bands is associated with a corresponding communication line of the communication cable 232. For example, in embodiments where the communication cable 232 consists of a trifilar, each of the three conductive bands 248 illustrated in FIG. 6 are connected to one of the conductors of the trifilar, for example by soldering each of the conductive bands to the respective conductor. Where the communication cable 232 includes optical communication line(s), the proximal portion 202 of the intravascular device 200 includes an optical connector in addition to or instead of one or more of the conductive bands 248. An insulating layer or sleeve 250 separates the conductive bands 248 from the core 246. In some instances, the insulating layer 250 is formed of polyimide.

As noted above, the proximal portion of core 238 is fixedly secured to the distal portion of core 246. In that regard, any suitable technique for securing the cores 238, 246 to one another may be used. In some embodiments, at least one of the cores includes a structural feature that is utilized to couple the cores together. In the illustrated embodiment, the core 238 includes an extension 252 that extends around a distal portion of the core 246. In some instances, the cores 238, 246 are soldered together. In some instances, an adhesive is utilized to secure the cores 238, 246 together. In some embodiments, combinations of structural interfaces, soldering, and/or adhesives are utilized to secure the cores 238, 246 together. In other instances, the core 226 is not fixedly secured to core 238. For example, in some instances and as noted above, the core 226 and the core 246 are fixedly secured to the hypotube 240 and the core 238 is positioned between the cores 226 and 246, which maintains the position of the core 238 between cores 226 and 246. In some embodiments, the core 246 is formed of a different material than the core 238. For example, in some instances the core 246 is formed of Nitinol and/or NiTiCo (nickel-titanium-cobalt alloy) and the core 238 is formed of stainless steel. In that regard, by utilizing a nitinol core within the conductive bands 248 instead of a stainless steel the likelihood of kinking is greatly reduced because of the increased flexibility of the nitinol core compared to a stainless steel core. In other instances, the core 238 and the core 246 are formed of the same material. In some instances the core 238 has a different profile than the core 246, such as a larger or smaller diameter and/or a non-circular cross-sectional profile.

Referring now to FIGS. 7-11, shown therein are various embodiments of proximal connectors according to the present disclosure. In particular, the embodiments of FIGS. 7-11 include flexible coil conductive bands that help to prevent kinking that can cause damage to the communication pathways of an intravascular device, such as communication cable 232 of intravascular device 200, by increasing the flexibility of the connecting portions of the intravascular device. The flexible coil conductive bands of the present disclosure also provide opportunities for reducing manufacturing costs and increasing the available space within the proximal portion of the device. For example, referring more specifically to FIG. 7, shown therein is a portion 260 of an intravascular device according to an embodiment of the present disclosure. As shown, the portion 260 includes electrical connectors 262, 264, and 266. In the illustrated embodiment of FIG. 7, each of the electrical connectors 262, 264, and 266 are formed of a wire coil, where the wire forming the coil has a circular cross-sectional profile. The wire is wound to have an outer diameter based on the desired outer diameter of the intravascular device. In that regard, the outer diameter of the coil may be equal to, slightly larger than, or slightly smaller than the desired outer diameter of the intravascular device. For example, in one embodiment of a 0.014" intravascular device, the coil has an outer diameter of 0.0142".

The electrical connectors 262, 264, and 266 are formed of a conductive material such as gold, an 80/20 platinum/iridium alloy, other platinum-iridium alloys, platinum-tungsten alloys, gold plated materials (e.g., stainless steel), other suitable conductive materials, and/or combinations thereof. In some embodiments, the electrical connectors 262, 264, and 266 include a stainless steel core with at least the outer surfaces plated with gold, copper, or other material having increased conductivity compared to stainless steel. An insulating portion 268 separates connector 262 from connector 264 and an insulating portion 270 separates connector 264 from connector 266. The electrical connectors 262, 264, and 266 and insulating portions 268 and 270 surround a central portion 272. In that regard, in some instances central portion 272 contains a core wire, communication cable(s), and/or other components of the intravascular device. In some specific embodiments, the central portion 272 includes at least a core wire and a trifilar. In that regard, each of the electrical connectors 262, 264, and 266 is connected to one of the conductors of the trifilar, for example, by soldering the conductor to the respective connector. In some embodiments, at least one of the electrical connectors 262, 264, and/or 266 does not have any insulating material positioned between it and the core. In that regard, in some such instances the electrical conductor(s) is soldered or otherwise secure to the core without any insulation material in between the element and the core. In one particular embodiment, the most proximal connector is secured to the core without any insulating material. Further, the connector secured to the core is a ground contact in some instances.

Referring now to FIG. 8, shown therein is a portion 280 of an intravascular device according to another embodiment of the present disclosure. As shown, the portion 280 includes electrical connectors 282, 284, and 286. In the illustrated embodiment of FIG. 8, each of the electrical connectors 282, 284, and 286 are formed of a wire coil, where the wire forming the coil has a rectangular cross-sectional profile. In some applications, the rectangular cross-sectional profile improves functionality of the connectors compared to the circular cross-sectional profile of FIG. 7 due to the more constant outer surface of the resulting connectors. Further, in some instances, the wire or ribbon forming the coil has a thickness of 0.001" or less. With a thickness of 0.001" or less, a significant increase in space within the coils is provided, which can be used to implement a core with larger diameter and/or other make assembling the proximal portion of the intravascular device easier. Further, in some instances the wire or ribbon forming the coil has a width of 0.005" or less. The wire or ribbon forming the coil is wound to have an outer diameter based on the desired outer diameter of the intravascular device. In that regard, the outer diameter of the coil may be equal to, slightly larger than, or slightly smaller than the desired outer diameter of the intravascular device. For example, in one embodiment of a 0.014" intravascular device, the coil has an outer diameter of 0.0142".

The electrical connectors 282, 284, and 286 are formed of a conductive material such as gold, an 80/20 platinum/iridium alloy, other platinum-iridium alloys, platinum-tungsten alloys, gold plated materials (e.g., stainless steel), other suitable conductive materials, and/or combinations thereof. In some embodiments, the electrical connectors 282, 284, and 286 include a stainless steel core with at least the outer surfaces plated with gold, copper, or other material having increased conductivity compared to stainless steel. An insulating portion 288 separates connector 282 from connector 284 and an insulating portion 290 separates connector 284 from connector 286. The electrical connectors 282, 284, and 286 and insulating portions 288 and 290 surround a central portion 292. In that regard, in some instances central portion 292 contains a core wire, communication cable(s), and/or other components of the intravascular device. In some specific embodiments, the central portion 292 includes at least a core wire and a trifilar. In that regard, each of the electrical connectors 282, 284, and 286 is connected to one of the conductors of the trifilar, for example, by soldering the conductor to the respective connector.

Referring now to FIG. 9, shown therein is a portion 300 of an intravascular device according to another embodiment of the present disclosure. As shown, the portion 300 includes electrical connectors 302, 304, and 306. In the illustrated embodiment of FIG. 9, each of the electrical connectors 302, 304, and 306 are formed of a wire coil, where the wire forming the coil has a semi-circular cross-sectional profile with the rounded portion of the profile forming the outer surface of the coil. The wire is wound to have an outer diameter based on the desired outer diameter of the intravascular device. In that regard, the outer diameter of the coil may be equal to, slightly larger than, or slightly smaller than the desired outer diameter of the intravascular device. For example, in one embodiment of a 0.014" intravascular device, the coil has an outer diameter of 0.0142".

The electrical connectors 302, 304, and 306 are formed of a conductive material such as gold, an 80/20 platinum/iridium alloy, other platinum-iridium alloys, platinum-tungsten alloys, gold plated materials (e.g., stainless steel), other suitable conductive materials, and/or combinations thereof. In some embodiments, the electrical connectors 302, 304, and 306 include a stainless steel core with at least the outer surfaces plated with gold, copper, or other material having increased conductivity compared to stainless steel. An insulating portion 308 separates connector 302 from connector 304 and an insulating portion 310 separates connector 304 from connector 306. The electrical connectors 302, 304, and 306 and insulating portions 308 and 310 surround a central portion 312. In that regard, in some instances central portion 312 contains a core wire, communication cable(s), and/or other components of the intravascular device. In some specific embodiments, the central portion 312 includes at least a core wire and a trifilar. In that regard, each of the electrical connectors 302, 304, and 306 is connected to one of the conductors of the trifilar, for example, by soldering the conductor to the respective connector.

Referring now to FIG. 10, shown therein is a portion 320 of an intravascular device according to another embodiment of the present disclosure. As shown, the portion 320 includes electrical connectors 322, 324, and 326. In the illustrated embodiment of FIG. 10, each of the electrical connectors 322, 324, and 326 are formed of a wire coil, where the wire forming the coil has a semi-circular cross-sectional profile with the flat portion of the profile forming the outer surface of the coil. In some applications, the using the flat portion as the outer surface of the coil improves functionality of the connectors compared to the using the rounded portion of the profile as the outer surface (as shown in FIG. 9) due to the more constant outer surface of the resulting connectors. The wire is wound to have an outer diameter based on the desired outer diameter of the intravascular device. In that regard, the outer diameter of the coil may be equal to, slightly larger than, or slightly smaller than the desired outer diameter of the intravascular device. For example, in one embodiment of a 0.014" intravascular device, the coil has an outer diameter of 0.0142".

The electrical connectors 302, 304, and 306 are formed of a conductive material such as gold, an 80/20 platinum/iridium alloy, other platinum-iridium alloys, platinum-tungsten alloys, gold plated materials (e.g., stainless steel), other suitable conductive materials, and/or combinations thereof. In some embodiments, the electrical connectors 322, 324, and 326 include a stainless steel core with at least the outer surfaces plated with gold, copper, or other material having increased conductivity compared to stainless steel. An insulating portion 328 separates connector 322 from connector 324 and an insulating portion 330 separates connector 324 from connector 326. The electrical connectors 322, 324, and 326 and insulating portions 328 and 330 surround a central portion 332. In that regard, in some instances central portion 332 contains a core wire, communication cable(s), and/or other components of the intravascular device. In some specific embodiments, the central portion 332 includes at least a core wire and a trifilar. In that regard, each of the electrical connectors 322, 324, and 326 is connected to one of the conductors of the trifilar, for example, by soldering the conductor to the respective connector.

Referring now to FIG. 11, shown therein is a diagrammatic cross-sectional close-up side view of a section of a proximal connector portion 340 of an intravascular device according to an embodiment of the present disclosure. In particular, FIG. 11 illustrates additional details of how a coil connector, such as those shown in FIGS. 7-10, may be incorporated into an intravascular device. In that regard, in the illustrated embodiment of FIG. 11, a coil 342 formed of a wire coil, where the wire forming the coil has a circular cross-sectional profile. The wire is wound to have an outer diameter based on the desired outer diameter of the intravascular device. In that regard, the outer diameter of the coil may be equal to, slightly larger than, or slightly smaller than the desired outer diameter of the intravascular device. For example, in one embodiment of a 0.014" intravascular device, the coil has an outer diameter of 0.0142". Further, the wire is wound such that there is sufficient spacing between adjacent windings of the coil 342 to facilitate soldering of a conductor positioned within the coil 342 to the coil. For example, as shown winding 344 and winding 346 as separated by space 348. Space 348 is between about 0.001" and about 0.0015" in some instances. Further, a conductor 350 is electrically coupled to the coil 342 at solder joint 352. In that regard, it is understood that multiple solder joints may be utilized in some instances. Insulating portions 356 and 358 separate the coil 342 from any adjacent coils. Further, an insulating layer 360 separates the coil 342, conductor 350, and solder joint 352 from a core 360, which is formed of a conductive material in some instances. In some instances, the insulating portions 356 and 358 and the insulating layer 360 are integrally formed. In other instances, the insulating portions 356 and 358 and the insulating layer 360 are formed separately.

In one particular embodiment, a shrink wrap is placed around the outer portion of the coil 342 (and any adjacent coils) and an insulating material is injected into the intravascular device and within the shrink wrap. The insulating material fills the space within the intravascular device around the insulating layer 360 and core 362. The close fit of the shrink wrap around the outer surface of the coil 342 prevents the insulating material from covering the outer conductive surface of the coil. Instead, the insulating material fills the spaces around the coil 342, thereby defining insulating portions 356 and 358, and any space between the coil 342 and the insulating layer 360, thereby forming insulating layer 364. In some instances, the insulating material is injected within the shrink wrap after the conductor 350 has been soldered to the coil 342. While the foregoing has been described with respect to the single coil 342 illustrated in FIG. 11, it is understood that the same arrangements and techniques for assembly may be utilized for two or more conductor coils of an intravascular device.

Referring now to FIGS. 12-16, shown therein are features related to forming a proximal connector portion of an intravascular device according to an embodiment of the present disclosure. Referring initially to FIG. 12, shown therein is tubing 400. In that regard, tubing 400 is a polymer tubing that includes a conductive coil embedded therein. The polymer used to form tubing 400 is polyimide in some instances, but may be another suitable insulating material in other instances. The conductive coil can be formed of any suitable conductive material, including gold, an 80/20 platinum/iridium alloy, other platinum-iridium alloys, platinum-tungsten alloys, gold plated materials (e.g., stainless steel), other suitable conductive materials, and/or combinations thereof. In some embodiments, tubing 400 is a polyimide tubing with an embedded spiral ribbon coil formed of a platinum-iridium compound. In one such embodiment, the platinum-iridium compound has a ration of platinum to iridium of approximately 80/20. As will be discussed in greater detail below, by exposing one or more portions of the embedded coil and electrically isolating the exposed portions from one another one or more conductive connectors can be defined in the tubing 400.

For example, as shown in FIG. 13, three conductive connectors 402, 404, and 406 have been formed by removing the surrounding polymer to expose the underlying coil. In that regard, the polymer is removed by laser ablation and/or chemical etching. As shown in FIG. 14, the polymer is removed such that the exposed portion of the coil 408 extends above the remaining polymer 410. In some instances, the polymer is removed such that the exposed coils 408 extend between about 0.0001" and about 0.0005" above the polymer. In one particular embodiment, the polymer is removed such that the exposed coils 408 extend approximately 0.0002" above the polymer. In other instances, the polymer is removed such that the exposed portion of the coil 408 and the remaining polymer 410 are substantially aligned with one another.

Figure 16:
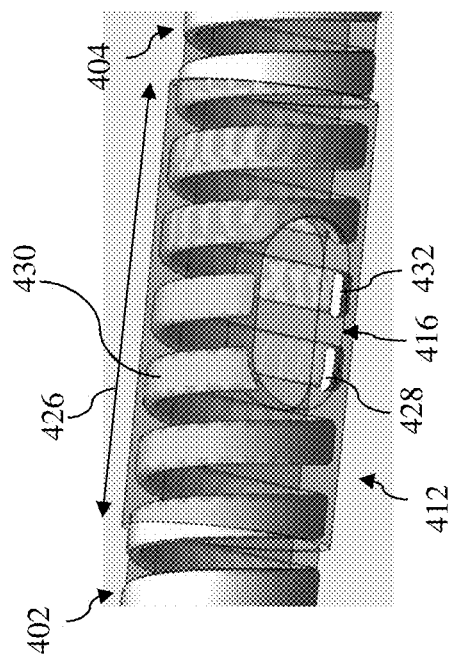
FIG. 16 is a diagrammatic close-up, partial phantom perspective view of an insulator portion of the proximal connector portion of FIG. 13.
Figure 15:
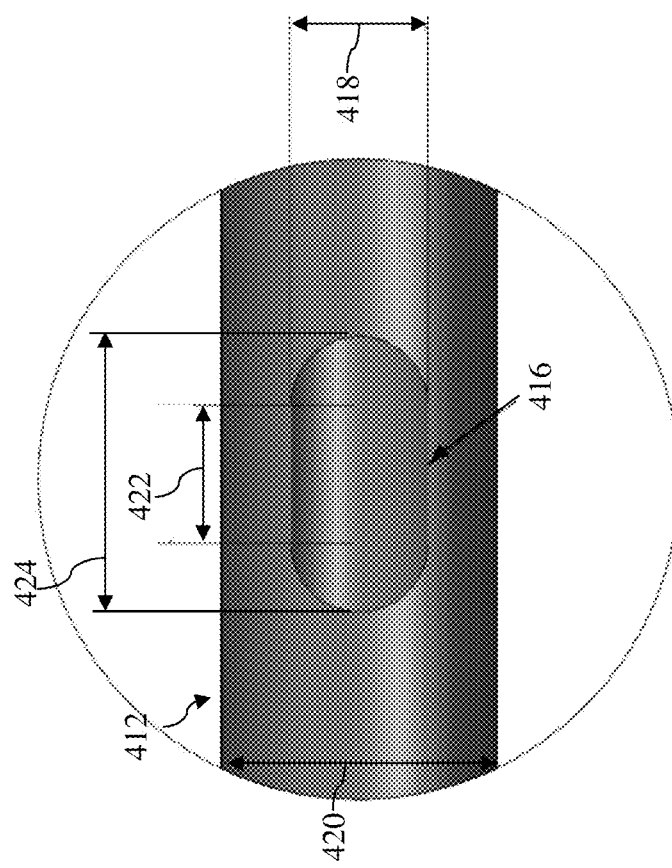
FIG. 15 is a diagrammatic close-up side view of an insulator portion of the proximal connector portion of FIG. 13.

Referring again to FIG. 13, in addition to exposing the connectors 402, 404, and 406, it is necessary to electrically isolate the connectors from one another. In that regard, the connectors 402, 404, and 406 are portions of the same coil embedded in tubing 400. Accordingly, it is necessary to separate the connectors 402, 404, and 406 from one another if they are to act as separate connectors. In that regard, isolation region 412 is positioned between connectors 402 and 404, while isolation region 414 is positioned between connectors 404 and 406. One technique for electrically isolating the connectors is illustrated by the detailed views of isolation region 412 provided in FIGS. 15 and 16. As shown in FIGS. 15 and 16, the isolation region 412 includes an opening 416 through a sidewall of the tubing 400. In that regard, in the illustrated embodiment the opening 416 is generally pill shaped, having elongated straight sides and rounded ends. In that regard, the opening 416 has a height 418 that is generally between about 25% and about 60% of a diameter 420 of the tubing 400. In one particular embodiment, the tubing 400 has an outer diameter of 0.014" and the opening 416 has a height 418 of 0.0070". In the illustrated embodiment, opening 416 also has a length 422 associated with the straight sides and an overall length 424 that includes the rounded end portions. Generally, the length 422 is between about 5% and about 90% of a total length 426 of the isolation region 412, while the length 424 is between about 10% and about 95% of the total length of the isolation region. In that regard, the size of the opening is dependent upon ensuring that at least one full coil wind has been separated so that there is definitive coil isolation. Accordingly, in some instances the opening has a minimum length of 2.5 times the coil pitch. For example, if the coil pitch is 0.005, then the opening length would be ~0.0125", thus guaranteeing that at least 1 full coil wind was separated.

As shown in FIG. 16, by creating the opening 416 in the side wall portions of the imbedded coil are also removed. In that regard, the opening 416 is created by laser cutting. In the illustrated embodiment, two windings of the coil have been cut. In other embodiments, one or more than two windings of the coil are cut within the isolation region 412. As a result of cutting two windings, three winding portions are created, namely coil portion 428 that is positioned within isolation portion 412, coil portion 430 that extends to the exposed portion that forms connector 402, and coil portion 432 that extends to the exposed portion that forms connector 404. In this manner, the coil portions 430 and 432 are electrically isolated from each other such that they can serve as separate electrical connectors for an intravascular device.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular device, comprising:
  a first flexible element;
  a second flexible element coupled to the first flexible element in a position proximal to the first flexible element;
  a third flexible element coupled to the second flexible element in a position proximal to the second flexible element;
  a distal core extending within the first flexible element;
  a mounting structure positioned within the second flexible element and fixedly secured to the distal core;
  at least one sensing component mounted to the mounting structure;
  a proximal core fixedly attached to the mounting structure and extending proximally from the mounting structure through the second and third flexible elements; and
  at least one conductor having a proximal section and a distal section, wherein the distal section of the at least one conductor is coupled to the at least one sensing component and the proximal section of the at least one conductor is coupled to at least one connector.

2. The intravascular device of claim 1, wherein the at least one connector comprises a coil.

3. The intravascular device of claim 2, wherein a wire forming the coil has a rectangular cross-sectional profile.

4. The intravascular device of claim 2, wherein a wire forming the coil has a circular cross-sectional profile.

5. The intravascular device of claim 2, wherein a wire forming the coil has a semi-circular cross-sectional profile with a rounded portion of the semi-circular cross-sectional profile extending outwardly.

6. The intravascular device of claim 2, wherein a wire forming the coil has a semi-circular cross-sectional profile with a rounded portion of the semi-circular cross-sectional profile extending inwardly.

7. The intravascular device of claim 2, wherein the proximal section of the at least one conductor is soldered to an inner portion of the coil.

8. The intravascular device of claim 2, wherein the coil is at least partially embedded within a polymer tubing.

9. The intravascular device of claim 1, wherein the second flexible element comprises a ribbon coil.

10. The intravascular device of claim 9, wherein the ribbon coil is embedded in a polymer tubing, the polymer tubing having a thickness between about 0.0005" and about 0.003".

11. The intravascular device of claim 9, wherein a section of the proximal core positioned within the ribbon coil is formed of nitinol.

12. The intravascular device of claim 11, wherein an insulating layer is positioned between the ribbon coil and the section of the proximal core positioned within the ribbon coil.

13. The intravascular device of claim 12, wherein the insulating layer is a polymer in which the ribbon coil is embedded.

14. The intravascular device of claim 1, wherein the proximal core includes a first section that is fixedly attached to the mounting structure and a second section extending proximally from the first section, wherein the first section is formed of a first material and the second section is formed of a second material different than the first material.

15. The intravascular device of claim 14, wherein the core further includes a third section extending proximally from the second section, wherein the third section is formed of a third material different than the second material.

16. The intravascular device of claim 15, wherein the third material is the same as the first material.

17. The intravascular device of claim 15, wherein the first material is a shape memory alloy, the second material is stainless steel, and the third material is a shape memory alloy.

18. The intravascular device of claim 1, wherein the at least one conductor consists of three conductors and the at least one connector consists of three connectors.

19. The intravascular device of claim 18, wherein the at least one conductor has a non-circular cross-sectional profile.

20. The intravascular device of claim 19, wherein the at least one conductor has a rounded, rectangular cross-sectional profile.

* * * * *